(12) United States Patent  
Carroll-Portillo

(10) Patent No.: US 11,702,766 B2
(45) Date of Patent: Jul. 18, 2023

(54) SYSTEMATIC CREATION OF FLUORESCENT FUSION POLYPEPTIDES

(71) Applicant: Sandia Biotech, Inc., Albuquerque, NM (US)

(72) Inventor: Amanda Carroll-Portillo, Albuquerque, NM (US)

(*) Notice: Subject to any disclaimer, the term of this patent is extended or adjusted under 35 U.S.C. 154(b) by 233 days.

(21) Appl. No.: 15/931,154

(22) Filed: May 13, 2020

(65) Prior Publication Data
US 2021/0010009 A1 Jan. 14, 2021

Related U.S. Application Data

(60) Provisional application No. 62/847,594, filed on May 14, 2019.

(51) Int. Cl.
C40B 50/06 (2006.01)
C12N 15/70 (2006.01)
C07K 16/00 (2006.01)

(52) U.S. Cl.
CPC .............. *C40B 50/06* (2013.01); *C07K 16/00* (2013.01); *C12N 15/70* (2013.01); *C07K 2317/24* (2013.01); *C07K 2317/55* (2013.01); *C07K 2317/622* (2013.01); *C07K 2319/60* (2013.01)

(58) Field of Classification Search
None
See application file for complete search history.

(56) References Cited

PUBLICATIONS

Thomas et al. (2015) Nature Methods vol. 12 pp. i to ii.*

* cited by examiner

*Primary Examiner* — Christian C Boesen
(74) *Attorney, Agent, or Firm* — V Gerald Grafe

(57) ABSTRACT

A method for creating a plasmid for use in producing a chimeric antibody, comprising (a) receiving a FAB region of the antibody; (b) receiving a fluorescent protein; (c) receiving a linker having length of at least 5 amino acids; (d) using the Gibson assembly process to join the FAB region, the fluorescent protein, and the linker into an expression plasmid.

13 Claims, 4 Drawing Sheets

Specification includes a Sequence Listing.

FIG. 4

SYSTEMATIC CREATION OF FLUORESCENT FUSION POLYPEPTIDES

TECHNICAL FIELD

The present application is related to the field of fluorescent proteins, more specifically to systematic creation of fluorescent fusion polypeptides.

BACKGROUND

Fluorescent protein fusion has long been a method of detection of biomolecules. A fluorescent protein, derived from an aquatic creature, is fused to a protein of interest to facilitate the protein's detection by visual and photometric means. Markiv et al demonstrated that a fluorescent protein could be genetically recombined with a scFv fragment, a single antigen recognition domain from an antibody. However, Markiv's teaching could not be consistently applied to any scFv from any antibody.

There remains a need for a method to consistently, successfully recombine any scFv with any fluorescent protein, that facilitates creation of an RFAB that is consistently expressed, as a predominantly soluble product.

SUMMARY OF INVENTION

Embodiments of the present invention provide methods to consistently, successfully recombine any scFv with any fluorescent protein, that facilitates creation of an RFAB that is consistently expressed, as a predominantly soluble product.

Embodiments of the present invention provide methods to consistently manufacture functional RFABs in large quantities. The various steps described provide methods of producing RFABs that is scaled to bulk manufacture for distribution and sale.

Embodiments of the present invention provide methods of manufacturing RFABs with a 2-week turnaround time, as illustrated in FIG. 2. Previous methods, such as shown in FIG. 1, require a minimum of 2 weeks to 4 weeks to generate the plasmids used in the production of the RFAB protein product.

Embodiments of the present invention provide methods to generate RFABs using Gibson assembly, a method of cloning DNA sequences or gene fragments into a plasmid usable by a bacterium to produce a desired protein. This process can require only a single step, in contrast to the 6 steps required to make the original RFAB, illustrated in FIG. 1.

Embodiments of the present invention provide methods to generate RFABs to any epitope, consistently by linker optimization. The method of Markiv et al. is hindered by sub-optimal linker sequences and un-optimized gene fragments, making the method applicable only to limited RFAB constructs. Methods provided by the present invention involve optimization of the linker sequences that enable a more stable pairing of the scFv portions of the RFAB when linked to the fluorescent protein portion. Such optimized linkers allow for the application of RFAB generation to any scFv, regardless of the class or species of the parent antibody's origin.

Embodiments of the present invention provide methods to optimize solubility by linker optimization. Apart from generation of more functional RFABs, linker optimization results in consistent solubility. More soluble RFABs are easier to extract and require less processing post-expression thus substantially reducing production time.

Embodiments of the present invention provide methods to efficiently produce RFABs, by creating scFv-containing plasmid libraries for subsequent incorporation of Fluorescent protein genes, by Gibson assembly.

An example embodiment of the present invention provides a method of creating a plasmid for use in producing a chimeric antibody, comprising: (a) receiving a FAB region of the antibody; (b) receiving a fluorescent protein; (c) receiving a linker having length of at least 5 amino acids; (d) using the Gibson assembly process to join the FAB region, the fluorescent protein, and the linker into an expression plasmid.

An example embodiment further comprises determining the difference in length between (a) the combined length of the Fab region and the fluorescent protein, and (b) the length of the prototype Fab used by Durvasula, and, (x) if the difference is less than or equal to 5 amino acids, then modifying the Fab region by shortening the length of the Fab region by the amount the difference is less than 5 amino acids and using a linker having a length of 5 amino acids; (y) if the difference greater than 5 amino acids, then using a linker having a length equal to the difference. An example length of linker region is 15.9 Angstroms. Linker regions of length 5 to 20 amino acids can be suitable. The overall length is tailored to match that of the prototype FAB described in US2011/0268661 A1 to Markiv, Durvasula, and Kang (herein "Durvasula", and the overall length the "Durvasula length"). US2011/0268661 A1 is incorporated herein by reference. In cases where the desired antibody/fluorescent protein is shorter than the Durvasula length, the linker can be made longer than that used in Durvasula; in cases where the desired antibody/fluorescent protein is longer than the Durvasula length, the linker can be made shorter than that used in Durvasula.

An example embodiment of the present invention provides a method of producing a chimeric antibody, comprising (a) creating a plasmid as described above, (b) inserting the plasmid into at least one of (y) chemically competent bacteria capable of protein expression from the plasmid, (z) electrocompetent bacteria capable of protein expression from the plasmid, and (c) using the bacteria to produce the chimeric antibody.

BRIEF DESCRIPTION OF THE DRAWINGS

FIG. 4 is an illustration of a process for determining linker length.

DESCRIPTION OF INVENTION

Figure 1:
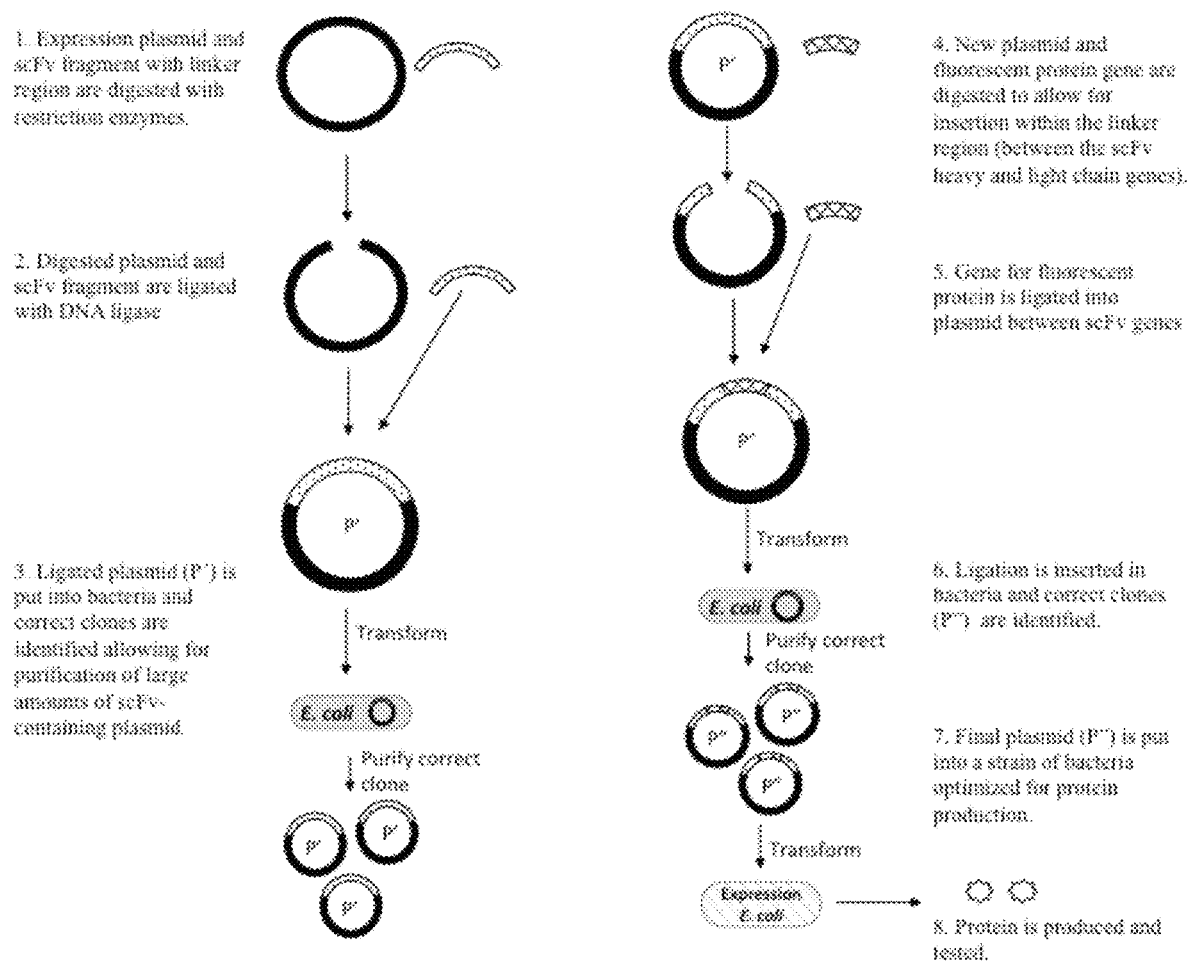
FIG. 1 is an illustration of RFAB production as contemplated in Markiv.

FIG. 1 is an illustration of RFAB production as contemplated in Markiv. RFABs were first invented by Markiv et al. in 2010. They employed an older method of restriction enzyme digestion with subsequent ligation of desired DNA fragments. Briefly, the recipient plasmid and scFv gene fragment (heavy and light chain separated by a 15 amino acid linker region) are digested with restriction enzymes specific for unique DNA sequences and digested fragments are ligated together. The resulting construct is then again digested within the linker region allowing for insertion of the gene for a fluorescent protein with matching digested ends. After a correct clone is identified, it is transformed into a bacterial host that is optimized for expression of Eukaryotic proteins.

Figure 2:
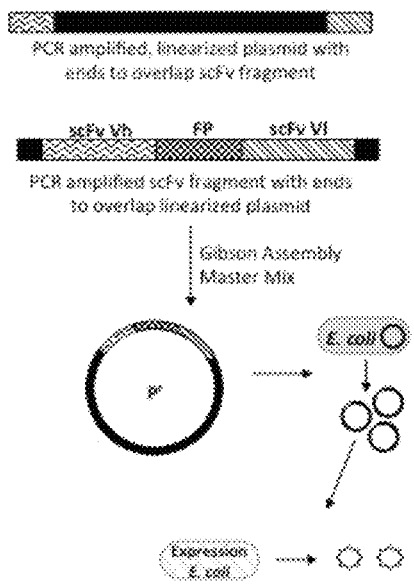
FIG. 2 is an illustration of Gibson assembly.
Figure 2:
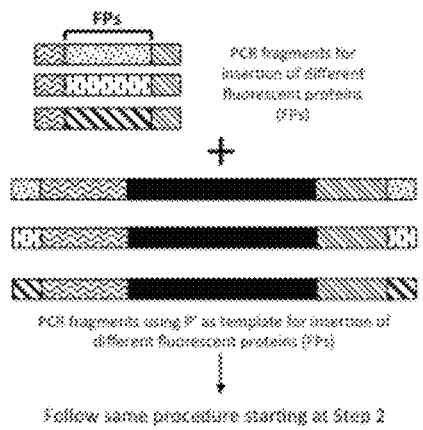

FIG. 2 is an illustration of Gibson assembly. Gibson Assembly allows the plasmid architect to bypass multiple digestion and ligation steps and bacterial propagation by performing multiple, simultaneous cloning steps with PCR templates containing overlapping regions of DNA.

Figure 3:
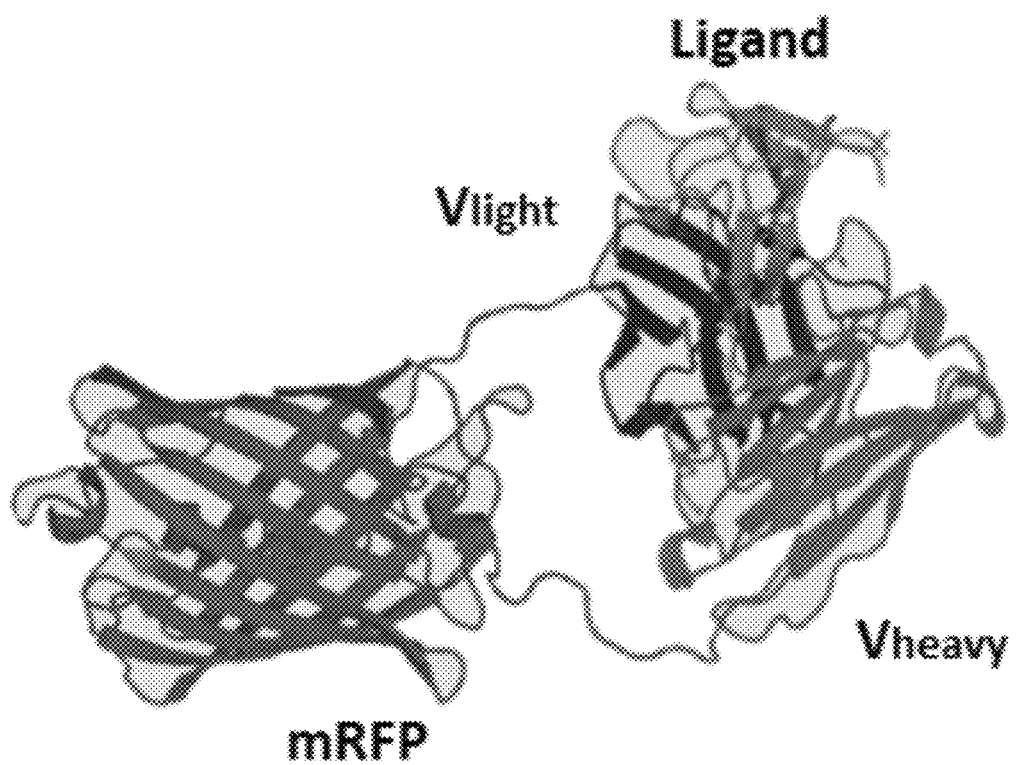
FIG. 3 is an illustration of binding of heavy and light chains.

FIG. 3 is an illustration of binding of heavy and light chains. The heavy and light chains are not directly bound to the fluorescent protein, in this example, mRFP. They are bound with linker regions comprising various amino acids, allowing the heavy and light regions to properly align and self-assemble. In an example embodiment of the RFAB, the linkers were of fixed length and, as the heavy and light chains of scFvs vary, linker length was not optimized to allow for proper alignment and folding of scFv regions in relation to the fluorophore in subsequent RFAB constructs. The present invention can provide methods that optimize linker length based on scFv fragment lengths for generation of new RFABs.

For every new RFAB, development of two linker regions can be required: a first linker linking the variable heavy chain fragment to the 5' end of the fluorophore and a second linker linking the variable light chain fragment to the 3' end of the fluorophore. The linker region can be important because enough space needs to exist between the fluorophore and each of the scFv fragments to allow for correct folding and alignment to occur. The linker region from example embodiments of the present invention involves use of a standard linker described in the literature consisting of four glycine residues and a single serine residue (GGGGS). In general for RFABs, this is the minimum linker that is used.

Figure 4:
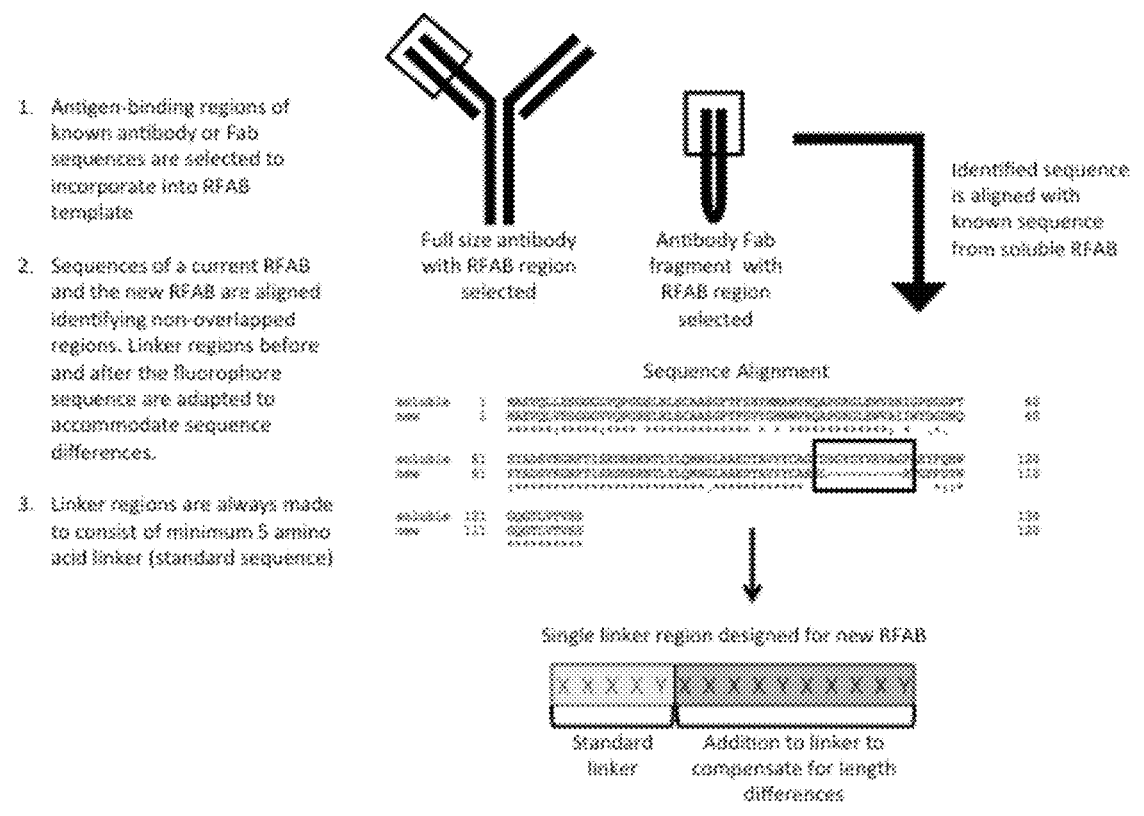

FIG. 4 is an illustration of a process for determining linker length. Minimum antigen binding domain regions within a FAB or full size antibody are determined through sequence analysis. These sequences are then aligned to a template RFAB, a current product that is completely soluble from a bacterial expression system. Upon alignment, the heavy and light variable regions are assessed for length as compared to the template. If the template is longer than the new RFAB, amino acids for an additional linker sequence (GnS where n=1 to 4) can be added to compensate for the difference. If the template is shorter, additional linker sequences of G4S can be added to both ends of the fluorophore and amino acids can then be removed to compensate for the length difference. In this manner, a minimum linker of G4S is always in place. Once the sequence has been determined, the RFAB can be moved to production as described in FIG. 2.

The following references, each of which is incorporated herein by reference, can facilitate understanding of the present invention.

Markiv et al, Expression of recombinant multi-coloured fluorescent antibodies in gor−/trxB *E. coli* cytoplasm BMC Biotechnology 2011, 11:117 doi:10.1186/1472-6750-11-117.

Markiv et al, Module based antibody engineering: A novel synthetic REDantibody, Journal of Immunological Methods 364 (2011) 40-49.

Gibson D G, Young L, Chuang R Y, Venter J C, Hutchison C A 3rd, Smith H O (2009). "Enzymatic assembly of DNA molecules up to several hundred kilobases". Nature Methods. 6 (5): 343-345. doi:10.1038/nmeth.1318. PMID 19363495.

Gibson D G. (2011). "Enzymatic assembly of overlapping DNA fragments". Methods in Enzymology. 498: 349-361. doi:10.1016/B978-0-12-385120-8.00015-2. PMID 21601685.

Wang S, Zheng C, Liu Y, Zheng H, Wang Z (2008). "Construction of multiform scFv antibodies using linker peptide". Journal of Genetics and Genomics. May; 35(5): 313-6. doi: 10.1016/C1673-8527(08)60045-4.

Bird R E, Hardman K D, Jocabson J W, Johnson S, Kaufman B M, Lee S M, Lee T, Pope S H, Riordan G S, Whitlow M. (1988). "Single-chain antigen-binding proteins". Science 242(2877):423-426.

Huston J S, Levinson D, Mudgett-Hunter M, Tai M S, Novotny J, Margolies M N, Ridge R J, Bruccoleri R E, Haber E, Crea R, et al. (1988). "Protein engineering of antibody binding sites: recovery of specific activity in an anti-digoxin shingle-chain Fv analogue produced in *Escherichia coli*." Proceedings of the National Academy of Sciences. 85(16):5879-5883.

Chappel J A, He M, Kang A S (1998). "Modulation of antibody display on M13 filamentous phage". Journal of Immunological Methods. 221(1-2):25-34.

Chappel J A, Rogers W O, Hoffman S L, Kang A S (2004). "Molecular dissection of the human antibody response to the structural repeat epitope of *Plasmodium falciparum* sporozoite from a protected donor." Malar Journal. 3:28.

Gu X, Jia X, Feng J, Shen B, Huang Y, Geng S, Sun Y, Wang Y, Li Y, Long M (2010). "Molecular modeling and affinity determination of scFv antibody: proper linker peptide enhances its activity". Annals of Biomedical Engineering. February; 38(2):537-49. doi: 10.1007/s10439-009-9810-2.

The present invention has been described in connection with various example embodiments. It will be understood that the above description is merely illustrative of the applications of the principles of the present invention, the scope of which is to be determined by the claims viewed in light of the specification. Other variants and modifications of the invention will be apparent to those skilled in the art.

The sequence listing in the ASCII text file named "sequence-listing-SA152-52001.txt", created 30 Sep. 2020, size 6K bytes, is incorporated herein by reference

I claim:

1. A method of creating a plasmid for use in producing a chimeric antibody, comprising:
   (a) receiving a FAB region of the antibody;
   (b) receiving a fluorescent protein;
   (c) receiving a linker having length of at least 5 amino acids (natural or unnatural, synthetic);
   (d) using the Gibson assembly process to join the FAB region, the fluorescent protein, and the linker into an expression plasmid.

2. The method of claim 1, further comprising using PCR to produce volumes of the FAB region, the fluorescent protein, and the linker for use in the Gibson assembly process.

3. The method of claim 1, wherein receiving a FAB region comprises determining if the combined length of the FAB region, the fluorescent protein, and the linker will exceed the Durvasula length, and, if so, modifying the FAB region such that the combined length will not exceed the Durvasula length.

4. The method of claim 1, wherein receiving a linker comprises determining the amount the length of (a) the combined length of the FAB region and the fluorescent protein, is less than (b) the Durvasula length, and receiving a linker whose length equals the determined amount.

5. The method of claim 1, further comprising determining the difference in length between (a) the combined length of the FAB region and the fluorescent protein, and (b) the Durvasula length, and,
   (x) if the difference is less than or equal to 5 amino acids, then modifying the FAB region by shortening the length of the FAB region by the amount the difference is less than 5 amino acids and using a linker having a length of 5 amino acids;
   (y) if the difference greater than 5 amino acids, then using a linker having a length equal to the difference.

6. A method of producing a chimeric antibody, comprising (a) creating a plasmid according to claim 1, (b) inserting the plasmid into at least one of (y) chemically competent bacteria capable of protein expression from the plasmid, (z)

electrocompetent bacteria capable of protein expression from the plasmid, and (c) using the bacteria to produce the chimeric antibody.

7. The method of claim 6 wherein step (b) comprises inserting the plasmid into chemically competent bacteria capable of protein expression from the plasmid.

8. The method of claim 6 wherein step (b) comprises inserting the plasmid into electrocompetent bacteria capable of protein expression from the plasmid.

9. The method of claim 6 wherein the bacteria comprises *E. coli*.

10. A method of producing a chimeric antibody, comprising (a) creating a plasmid according to claim 5, (b) inserting the plasmid into at least one of (y) chemically competent bacteria capable of protein expression from the plasmid, (z) electrocompetent bacteria capable of protein expression from the plasmid, and (c) using the bacteria to produce the chimeric antibody.

11. The method of claim 1, wherein the linker comprises at least one natural amino acid.

12. The method of claim 1, wherein the linker comprises at least one synthetic amino acid.

13. The method of claim 1, wherein the linker comprises at least one natural amino acid and at least one synthetic amino acid.

\* \* \* \* \*

SEQUENCE LISTING

<160> NUMBER OF SEQ ID NOS: 1

<210> SEQ ID NO 1
<211> LENGTH: 1485
<212> TYPE: DNA
<213> ORGANISM: Artificial Sequence
<220> FEATURE:
<223> OTHER INFORMATION: synthesized

<400> SEQUENCE: 1

```
-continued atg gct gaa gtc cag ctg caa cag agt gga ccg gaa ctt gtc aag        45
Met Ala Glu Val Gln Leu Gln Gln Ser Gly Pro Glu Leu Val Lys
 1               5                  10                  15 cca ggt gca tct atg aag ata agc tgt aag gca agc ggg tat agt        90
Pro Gly Ala Ser Met Lys Ile Ser Cys Lys Ala Ser Gly Tyr Ser
                20                  25                  30 ttt act ggt tat aca atg aac tgg gtc aaa caa agt cat ggt aag       135
Phe Thr Gly Tyr Thr Met Asn Trp Val Lys Gln Ser His Gly Lys
            35                  40                  45 aat tta gag tgg atg ggt ttg att aac ccg tat aag ggt gtc agc       180
Asn Leu Glu Trp Met Gly Leu Ile Asn Pro Tyr Lys Gly Val Ser
        50                  55                  60 acg tac aac cag aaa ttc aag gat aaa gca acg tta act gta gat       225
Thr Tyr Asn Gln Lys Phe Lys Asp Lys Ala Thr Leu Thr Val Asp
    65                  70                  75 aag tcg tcg agt acg gcg tat atg gag tta tta agt tta acc tct       270
Lys Ser Ser Ser Thr Ala Tyr Met Glu Leu Leu Ser Leu Thr Ser
80                  85                  90 gag gac agc gcc gtg tac tac tgt gca aga tct ggt tat tac ggg       315
Glu Asp Ser Ala Val Tyr Tyr Cys Ala Arg Ser Gly Tyr Tyr Gly
            95                 100                 105 gac tca gat tgg tat ttt gac gtg tgg gga caa ggg aca act ctt       360
Asp Ser Asp Trp Tyr Phe Asp Val Trp Gly Gln Gly Thr Thr Leu
        110                 115                 120 acc gtg ttt agc ggt ggt ggc ggt tca atg ggc aaa gga gaa gaa       405
Thr Val Phe Ser Gly Gly Gly Gly Ser Met Gly Lys Gly Glu Glu
    125                 130                 135 ctt ttc act gga gtt gtc cca att ctt gtt gaa tta gat ggt gat       450
Leu Phe Thr Gly Val Val Pro Ile Leu Val Glu Leu Asp Gly Asp
140                 145                 150 gtt aat ggg cac aaa ttt tct gtc aga gga gag ggt gaa ggt gat       495
Val Asn Gly His Lys Phe Ser Val Arg Gly Glu Gly Glu Gly Asp
            155                 160                 165 gct aca aac gga aaa ctc acc ctt aaa ttt att tgc act act gga       540
Ala Thr Asn Gly Lys Leu Thr Leu Lys Phe Ile Cys Thr Thr Gly
        170                 175                 180 aaa cta cct gtt cca tgg cca aca ctt gtc act act ctg acc tat       585
Lys Leu Pro Val Pro Trp Pro Thr Leu Val Thr Thr Leu Thr Tyr
    185                 190                 195 ggt gtt caa tgc ttt tcc cgt tat ccg gat cac atg aaa cgg cat       630
Gly Val Gln Cys Phe Ser Arg Tyr Pro Asp His Met Lys Arg His
200                 205                 210 gac ttt ttc aag agt gcc atg ccc gaa ggt tat gta cag gaa cgc       675
Asp Phe Phe Lys Ser Ala Met Pro Glu Gly Tyr Val Gln Glu Arg
            215                 220                 225 act ata tct ttc aaa gat gac ggg acc tac aag acg cgt gct gaa       720
Thr Ile Ser Phe Lys Asp Asp Gly Thr Tyr Lys Thr Arg Ala Glu
        230                 235                 240 gtc aag ttt gaa ggt gat acc ctt gtt aat cgt atc gag tta aaa       765
Val Lys Phe Glu Gly Asp Thr Leu Val Asn Arg Ile Glu Leu Lys
    245                 250                 255 ggt att gat ttt aaa gaa gat gga aac att ctc gga cac aaa ctc       810
Gly Ile Asp Phe Lys Glu Asp Gly Asn Ile Leu Gly His Lys Leu
260                 265                 270 gag tac aac ttt aac tca cac aat gta tac atc acg gca gac aaa       855
Glu Tyr Asn Phe Asn Ser His Asn Val Tyr Ile Thr Ala Asp Lys
            275                 280                 285 caa aag aat gga atc aaa gct aac ttc aaa att cgc cac aac gtt       900
Gln Lys Asn Gly Ile Lys Ala Asn Phe Lys Ile Arg His Asn Val
```

```
                    290                 295                 300
gaa gat ggt tcc gtt caa cta gca gac cat tat caa caa aat act         945
Glu Asp Gly Ser Val Gln Leu Ala Asp His Tyr Gln Gln Asn Thr
                    305                 310                 315 cca att ggc gat ggc cct gtc ctt tta cca gac aac cat tac ctg         990
Pro Ile Gly Asp Gly Pro Val Leu Leu Pro Asp Asn His Tyr Leu
                    320                 325                 330 tcg aca caa tct gtc ctt tcg aaa gat ccc aac gaa aag cgt gac        1035
Ser Thr Gln Ser Val Leu Ser Lys Asp Pro Asn Glu Lys Arg Asp
                    335                 340                 345 cac atg gtc ctt ctt gag ttt gta act gct gct ggg att aca cat        1080
His Met Val Leu Leu Glu Phe Val Thr Ala Ala Gly Ile Thr His
                    350                 355                 360 ggc atg gat gag ctc tac aaa gga tcc gga ggc gga tcg gat            1125
Gly Met Asp Glu Leu Tyr Lys Gly Ser Gly Gly Gly Ser Asp
                    365                 370                 375 atc caa atg act caa acg acg agc tcc ctt agt gcg tcg ctt ggc        1170
Ile Gln Met Thr Gln Thr Thr Ser Ser Leu Ser Ala Ser Leu Gly
                    380                 385                 390 gac cgc gtc act atc tct tgt cgg gca agt caa gac ata aga aat        1215
Asp Arg Val Thr Ile Ser Cys Arg Ala Ser Gln Asp Ile Arg Asn
                    395                 400                 405 tac ctg aat tgg tac caa cag aaa cct gat ggc aca gta aaa ctg        1260
Tyr Leu Asn Trp Tyr Gln Gln Lys Pro Asp Gly Thr Val Lys Leu
                    410                 415                 420 ctg atc tac tac act tcg cgg ctg cat agc ggt gtg cca agc aaa        1305
Leu Ile Tyr Tyr Thr Ser Arg Leu His Ser Gly Val Pro Ser Lys
                    425                 430                 435 ttt agc ggt tcc gga tca gga acg gac tac tca tta aca atc tct        1350
Phe Ser Gly Ser Gly Ser Gly Thr Asp Tyr Ser Leu Thr Ile Ser
                    440                 445                 450 aac tta gaa cag gag gat ata gcc acc tat ttt tgt caa caa ggg        1395
Asn Leu Glu Gln Glu Asp Ile Ala Thr Tyr Phe Cys Gln Gln Gly
                    455                 460                 465 aat act ctg ccg tgg acc ttt gcc gga gga aca aaa ctg gag att        1440
Asn Thr Leu Pro Trp Thr Phe Ala Gly Gly Thr Lys Leu Glu Ile
                    470                 475                 480 aag cgc gcg gat gcg gcc gca ctc gag cac cac cac cac cac cac        1485
Lys Arg Ala Asp Ala Ala Ala Leu Glu His His His His His His
                    485                 490                 495
```